US008931479B2

(12) United States Patent
Keegstra et al.

(10) Patent No.: US 8,931,479 B2
(45) Date of Patent: *Jan. 13, 2015

(54) DRY-POWDER INHALER

(75) Inventors: Johan René Keegstra, Alkmaar (NL); Krijn Franciscus Marie Zuyderhoudt, Leiden (NL); Johannes Wilhelmus Maria Sanders, Hoofddorp (NL)

(73) Assignee: Norton Healthcare Limited, London (GB)

( * ) Notice: Subject to any disclaimer, the term of this patent is extended or adjusted under 35 U.S.C. 154(b) by 551 days.

This patent is subject to a terminal disclaimer.

(21) Appl. No.: 13/321,077

(22) PCT Filed: May 17, 2010

(86) PCT No.: PCT/EP2010/002993
§ 371 (c)(1),
(2), (4) Date: Jan. 3, 2012

(87) PCT Pub. No.: WO2010/136134
PCT Pub. Date: Dec. 2, 2010

(65) Prior Publication Data
US 2012/0097161 A1    Apr. 26, 2012

Related U.S. Application Data

(60) Provisional application No. 61/179,167, filed on May 18, 2009.

(51) Int. Cl.
*A61M 15/00*    (2006.01)
(52) U.S. Cl.
CPC ......... *A61M 15/0045* (2013.01); *A61M 15/043* (2014.02); *A61M 15/0051* (2014.02); *A61M 15/0055* (2014.02); *A61M 15/0075* (2014.02); *A61M 2202/064* (2013.01)
USPC ................................ 128/203.15; 128/203.12

(58) Field of Classification Search
USPC ............. 128/200.24, 203.12, 203.15, 203.21, 128/205.23
See application file for complete search history.

(56) References Cited

U.S. PATENT DOCUMENTS

| 5,590,645 A | 1/1997 | Davies et al. |
| 2006/0196504 A1 | 9/2006 | Augustyn et al. |

(Continued)

FOREIGN PATENT DOCUMENTS

| JP | 2006528500 A | 12/2006 |
| JP | 2007526562 A | 9/2007 |

(Continued)

OTHER PUBLICATIONS

Japanese Office Action w/English translation, dated Feb. 19, 2014, corresponding to counterpart Japanese Patent Application No. 2012-511180.

*Primary Examiner* — Annette Dixon
(74) *Attorney, Agent, or Firm* — RatnerPrestia

(57) ABSTRACT

An inhaler for delivering dry-powder medicament to a patient from an open blister pocket of a blister pack. The blister pack has a plurality of blister pockets spaced apart in a length direction of the pack and each containing a measured dose of the medicament. The inhaler includes a housing for enclosing used and unused portions of the blister pack together with a medicament dispensing mechanism for opening the blister pockets of the blister pack. The inhaler also includes a manifold through which air can be drawn in use of the inhaler, the manifold including an air inlet for receiving external air, at least one medicament aperture for communicating with an opened pocket of the blister pack to enable entrainment of the medicament by the air drawn through the manifold, and an air outlet for delivery of the entrained medicament to the patient.

43 Claims, 8 Drawing Sheets

(56) References Cited

U.S. PATENT DOCUMENTS

| | | |
|---|---|---|
| 2008/0041368 A1 | 2/2008 | Jones et al. |
| 2008/0196718 A1 | 8/2008 | Connell et al. |
| 2008/0308102 A1 | 12/2008 | Davies et al. |
| 2009/0139516 A1 | 6/2009 | Augustyn et al. |
| 2010/0000528 A1* | 1/2010 | Palmer et al. ............ 128/203.15 |
| 2010/0000529 A1* | 1/2010 | Prime et al. .............. 128/203.15 |
| 2012/0097162 A1* | 4/2012 | Keegstra et al. ......... 128/203.15 |
| 2012/0167881 A1* | 7/2012 | Keegstra et al. ......... 128/203.15 |

FOREIGN PATENT DOCUMENTS

| | | |
|---|---|---|
| JP | 2009502287 A | 1/2009 |
| JP | 2009518093 A | 5/2009 |
| WO | WO2005/079727 A2 | 9/2005 |

* cited by examiner

DRY-POWDER INHALER

CROSS-REFERENCE TO RELATED APPLICATIONS

This application is a U.S. National Phase of PCT Application No. PCT/EP2010/002993, filed May 17, 2010, which claims priority to U.S. Provisional Patent Application No. 61/179,167, filed May 18, 2009, both of which are incorporated by reference herein in their entirety.

FIELD OF THE INVENTION

This invention relates to a dry-powder inhaler for delivering dry-powder medicament doses to a patient. More particularly, the invention relates to an inhaler of this type in which the medicament doses are stored in a medicament carrier in the form of a blister pack.

BACKGROUND OF THE INVENTION

Inhalers for delivering medicament to a patient by inhalation are known. Such devices include metered dose inhalers and dry-powder inhalers.

Metered-dose inhalers typically comprise a vessel, said vessel containing at least a pressurised propellant and a medicament, and a metering valve and some form of actuator for dispensing doses of the liquid medicament as an aerosol. In contrast, dry-powder inhalers comprise a supply of dry-powder medicament together with means for aerosoling and deagglomerating the medicament into a form suitable for delivery to a patient.

Dry-powder inhalers are generally considered to be easier to use than metered-dose inhalers because of difficulties in coordinating actuation of the metering valve of the metered-dose inhaler with a patent's inspiration. Moreover, since the medicament is aerosolised and delivered using the patient's inspirational airflow, dry-powder inhalers do not require a propellant.

It has been recognised that, in order to aerosolise and deliver a consistent dose of dry-powder medicament in an effective manner, the moisture content of the medicament must be carefully controlled. In dry-powder inhalers this can be conveniently achieved by storing doses of the medicament in the blisters of a sealed blister pack. In use of such devices, a dose of the medicament is typically liberated by piercing, bursting or peeling off a portion of a cover sheet of the blister pack immediately before the dose is to be delivered to the patient for inhalation.

A known dry-powder inhaler of this type, in which doses of the medicament are stored in a blister pack, is disclosed in U.S. Pat. No. 5,590,645. The blister pack of this inhaler is formed as a flexible elongate strip, and comprises a base sheet having a plurality of recesses spaced along its length and a cover sheet hermetically but peelably sealed to the base sheet to define a plurality of blister pockets each containing an identical dose of the medicament.

The inhaler of U.S. Pat. No. 5,590,645 comprises a medicament dispensing mechanism which is arranged to peel a portion of the cover sheet away from the base sheet of the blister pack to thereby open a blister pocket each time the inhaler is actuated. The mechanism includes a blister pack indexing means for moving the opened pocket into registration with medicament holes formed in a manifold of the inhaler, the manifold being in fluid communication with a mouthpiece through which the patient can inhale. An unused portion of the blister pack and used potions of the base sheet and cover sheet are stored within the body of the inhaler.

In use of the above-described inhaler, the patient exposes the mouthpiece by rotating a cover relative to the body of the inhaler, and operates a trigger to actuate the medicament dispensing mechanism. The patient then inhales through the mouthpiece to draw air through the manifold from within the body of the inhaler. The airflow passing through the mouthpiece and the manifold entrains the dry-powder medicament contained within the opened blister pocket, which medicament is delivered to the patient in aerosolised form. The trigger and the cover of the inhaler are then returned to their original positions to reset the medicament dispensing mechanism in preparation for a subsequent use.

Although dry-powder inhalers of the type disclosed in U.S. Pat. No. 5,590,645 exhibit improved consistency in the size of the doses which are delivered to the patient, there remains a need for inhalers having improved dosing consistency. There is a particular need for inhalers in which the risk of overdosing can be minimised.

SUMMARY OF THE INVENTION

According to the invention there is provided an inhaler for delivering dry-powder medicament to a patient from an open blister pocket of a blister pack, the blister pack having a plurality of blister pockets spaced apart in a length direction of the pack and each containing a measured dose of the medicament, the inhaler comprising:
  a housing for enclosing used and unused portions of the blister pack together with a medicament dispensing mechanism for opening the blister pockets of the blister pack; and
  a manifold through which air can be drawn in use of the inhaler, the manifold comprising an air inlet for receiving external air, at least one medicament aperture for communicating with an opened pocket of the blister pack to enable entrainment of the medicament by the air drawn through the manifold, and an air outlet for delivery of the entrained medicament to the patient,
  wherein the manifold and a part of the housing are provided as a unitary moulded plastics component, and wherein the unitary component defines, in use, at least a portion of the outer surface of the inhaler in which the air inlet is arranged.

By providing the manifold having the air inlet and the part of the housing which defines an outer surface of the inhaler (in which the air inlet is arranged) as a unitary component, the risk of air being drawn into the manifold from within the inhaler housing can be minimised. It is desirable to avoid air from within the housing from being drawn into the manifold because such air may entrain loose medicament in the housing left over from previous actuations of the medicament dispensing mechanism, for example medicament which has not been inhaled or has been incompletely inhaled.

Preferably, the air inlet of the manifold defines the sole point for entry for external air into the inhaler, and/or the manifold is arranged such that, in use, air is drawn into the manifold solely through the air inlet, that is to say air is not drawn through any component of the inhaler other that the unitary component (and of course an opened blister pocket of the blister pack).

The unitary component defines, in use, at least a part of the outer surface of the inhaler surrounding the air inlet of the manifold, and may in fact define the entire outer surface of the inhaler surrounding the air inlet. In other embodiments, the outer surface surrounding the air inlet may in part be defined by other components such as covers, mouthpiece cover and mouthpiece inserts, etc.

The air inlet of the manifold may have an elongate cross-sectional shape, and the cross-sectional area of the manifold may reduce in the airflow direction. With such an arrangement the airflow velocity within the manifold is lowest at the air opening, and this may reduce the risk of loose powder or other contaminants being entrained around the air inlet.

The manifold may comprise at least two medicament apertures arranged sequentially in the airflow direction of the manifold, namely a first medicament aperture for the flow of air from the manifold into the opened blister pocket and a second medicament aperture for the flow of the entrained medicament from the opened blister pocket into the manifold. In this case, the geometry of the manifold may be specifically adapted to direct air from the air inlet into the opened blister pocket through the first medicament aperture and to direct the entrained medicament from the opened blister pocket into the manifold through the second medicament aperture.

The geometry of the manifold may be adapted to provide the required flows by providing means for restricting airflow in the manifold between the first and second medicament apertures, for example by providing a localised reduction in the cross-sectional area of the manifold. Such a localised reduction in the cross-sectional area of the manifold may take the form of a protrusion in a wall of the manifold opposite to the medicament holes.

The unitary component may further define a mouthpiece arranged to receive, in use, the entrained medicament from the air outlet of the manifold. An end of the mouthpiece may be provided with a mouthpiece cover or insert having a surface around which a patient may comfortably seal his lips.

The manifold and the mouthpiece may be arranged such that the airflow direction in the mouthpiece is substantially perpendicular to the airflow direction in the manifold, with a bend in the airflow located adjacent to the second medicament aperture such that entrained medicament can be delivered to the patient from the opened blister pocket along a substantially straight path.

The cross-sectional area of the mouthpiece may increase in the airflow direction, and tapered walls of the mouthpiece may be provided with a plurality of airflow diversion holes. The airflow diversion holes are preferably in fluid communication with the manifold such that, in use, air from the manifold is drawn through the airflow diversion holes. The airflow diversion holes may be arranged such that, in use, air is drawn through the holes in a direction substantially parallel to a central axis of the mouthpiece (an acute angle to the walls of the mouthpiece) for preventing excessive transverse spreading of the entrained medicament in the mouthpiece.

The at least one medicament aperture may provided with at least one obstacle to promote de-agglomerating the entrained medicament. The obstacle may, in effect, serve as a divider to divide each aperture into a plurality of sub-apertures. In use, agglomerated particles of medicament collide with the divider which leads to their break-up.

In embodiments, the unitary component is a moulded component, and may be formed of a plastics material. Suitable materials for the unitary component may be selected from the group consisting of polyolefins, including polyethylene, in particular high density polyethylene (HDPE), and polypropylene; polyesters, including polyethylene terephthalate; polyamides, including nylons; thermosetting polymers, including urea-formaldehyde, melamine, epoxy resins and polyimides; and mixtures or copolymers thereof.

The inhaler housing may comprise a pair of outer housing members defining an outer shape of the inhaler. One of these pair of outer housing members may be the unitary component described above.

The inhaler may further comprise a dose counter, wherein the dose counter comprises:
 a display aperture formed in one of the pair of outer housing members;
 a display element having dose counting indicia, the display element being rotatably mounted inside the housing such that a succession of the dose counting indicia are sequentially visible through the display aperture as the display element is rotated about an axis of the outer shape of the inhaler; and
 a driving means for incrementally rotating the display element in response to actuation of the medicament dispensing mechanism.

Such a dose counter may enable a patient to reliably determine how many times the medicament dispensing mechanism has been actuated, which can help to avoid over-dosing or the inhalation of multiple doses.

The display aperture formed in the outer housing member may be provided with a magnifying lens arranged to magnify the dose counting indicia of the display element. In this way, information from the dose counter may be more easily seen by a patient and/or a greater number of indicia may be provided. The magnifying lens may be a convex lens formed, for example, from a transparent plastics material.

As the dose counting indicia of the display element are magnified, their actual size may be relatively small, so that the display element can be provided with a large number of indicia, and such that only one display element may be needed. In this case, complicated mechanisms for coupling multiple rotatably mounted display elements can be avoided.

The dose counting indicia of the display element may include a unique indicium for display after each and every actuation of the medicament dispensing mechanism. At least 10, preferably at least 20, more preferably at least 50, even more preferably at least 60, unique dose counting indicia may be provided, and the indicia may comprise numerals, preferably Arabic numerals. Each dose counting indicium may be representative of a number of doses dispensed by or remaining in the inhaler.

In embodiments, the inhaler housing further comprises an inner housing member arranged within the pair of outer housing members described above.

In embodiments, the inhaler may further comprise the medicament dispensing mechanism for opening the blister pockets of the blister pack. This mechanism may form a part of a replaceable cartridge insertable into the inhaler housing, or the mechanism may be a fixed and permanent part of the inhaler.

Embodiments of the inhaler may be suitable for delivering medicament from a blister pack in the form of a flexible elongate strip comprising a base sheet having a plurality of recesses spaced along its length and a cover sheet peelably sealed to the base sheet to define the plurality of blister pockets. In this case, the medicament dispensing mechanism of the inhaler comprises means for peeling the cover sheet away from the base sheet of the blister pack. A peeling-type mechanism may be preferred to piercing or bursting-type mechanisms because it may provide an inhaler which delivers greater dosing consistency.

The medicament dispensing mechanism may comprise a driven cover sheet winding wheel for winding up and applying a tension to the used portion of the cover sheet and a guide surface for guiding the cover sheet of the unused portion of the blister pack. In this case, an end of the guide surface is arranged adjacent to an outer side surface of the manifold and defines a peeling edge. In use of the inhaler, the cover sheet is peeled away from the base sheet at the peeling edge and the used portion of the cover sheet is passed between the peeling edge and the outer side surface of the manifold, with an opened blister pocket moving into registration with the at least one medicament aperture of the manifold.

In embodiments, the guide surface is defined by the inner housing member, such that the manifold and the guide surface are defined by separate components of the inhaler. Preferably, in use the outer side surface of the manifold splits the base sheet from the cover sheet.

During assembly of the inhaler, the used portion of the cover sheet is threaded through a gap between the peeling edge and the side surface of the manifold and then engaged with the cover sheet winding wheel. By providing an inhaler in which the guide surface and the manifold are defined by separate components, the width of the gap between the peeling edge and the manifold in the assembled inhaler can be minimised. For example, the used portion of the cover sheet may be threaded through the gap prior to assembly of the components and while the gap is relatively wide, and then the components may be assembled with the blister pack into the inhaler with the gap having a reduced width, for example only marginally wider than the thickness of the cover sheet. Typically, in use, the outer side surface of the manifold and the peeling edge are arranged so as to define a gap sufficient to enable the cover sheet to pass therethrough, said gap being less than or equal to about 1 mm, preferably less than or equal to about 0.8 mm, more preferably less than or equal to about 0.4 mm. Preferably, said gap is from about 0.1 mm to about 0.8 mm, preferably from about 0.2 mm to about 0.6 mm, more preferably from about 0.2 to about 0.4 mm. Preferably, said gap is less than half the individual width of the recesses in the base sheet, more preferably less than a quarter of the individual width of the recesses in the base sheet and even more preferably less than one eighth of the individual width of the recesses in the base sheet. By minimising the width of the gap, the risk of medicament being lost from an opened blister pocket during use of the inhaler, as the blister pocket is moved from the peeling edge into registration with the at least one medicament hole of the manifold, is minimised. In this way, underdosing (and possible subsequent overdosing) may be avoided, the likelihood of the device jamming is also reduced and the device may be tuned so as to accommodate different formulation characteristics more easily.

In embodiments, the inner housing member and the pair of outer housing members may comprise means for locating the inner housing member relative to the pair of outer housing members. The means for locating may include engagement tabs and recesses formed in the inner housing member and the pair of outer housing members, the engagement tabs and recesses being arranged to engage with each other to fix the location of the inner housing member relative to the pair of outer housing members.

In embodiments, the inner housing member may define internal transverse walls extending in the width direction of the blister pack for isolating the used portion of the cover sheet from the unused portion of the blister pack. Since the used portion of the cover sheet may carry a residual amount of medicament left over from previous actuations of the medicament dispensing mechanism, the risk of overdosing can be reduced by isolating the used cover sheet from the unused portion of the blister pack.

By "isolating", it is meant that the internal transverse walls serve to make it more difficult for medicament from the used portion of the cover sheet to contaminate the unused portion of the blister pack.

The medicament dispensing mechanism may further comprise a driven base sheet winding wheel for winding up the used portion of the base sheet, and the inner housing member may further define internal transverse walls extending in the width direction of the blister pack for isolating the used portion of the base sheet from the unused portion of the blister pack. Like the used portion of the covers sheet, the used portion of the base sheet may also carry residual medicament and it is therefore advantageous to isolate this from the unused portion of the blister pack.

The internal transverse walls of the inner housing member may define separate compartments for accommodating the used portion of the cover sheet and the used portion of the base sheet, the separate compartments being arranged to contain loose medicament, that is to say prevent loose medicament from contaminating the unused portion of the blister pack. The internal transverse walls of the inner housing member may further define a separate compartment for accommodating the unused portion of the blister pack. Surfaces of the inner housing member and one of the pair of outer housing members may be arranged to substantially enclose the unused portion of the blister pack.

The internal transverse walls may extend in a perpendicular direction from a base surface of the inner housing member, the base surface of the inner housing member being arranged to support a side edge of the unused portion of the blister pack, which unused portion may be coiled up. One of the pair of outer housing members may be arranged to support an opposite side edge of the unused portion of the blister pack.

In embodiments, the medicament dispensing mechanism may comprise means for longitudinally indexing the blister pack in response to each actuation of the medicament dispensing mechanism, the blister pack being indexed by a distance equal to the pitch between blister pockets, such that each actuation causes a blister to be brought into registration with the at least one medicament apertures of the manifold. The means for indexing may comprise a driven indexing wheel having recesses adapted to receive the base sheet of the blister pack, the recessed wheel being arranged to turn by a predetermined angle in response to each actuation of the medicament dispensing mechanism. The indexing wheel may be arranged to face the guide surface of the medicament dispensing mechanism.

The inhaler may comprise a trigger control for actuating the medicament dispensing mechanism and/or a cover rotatable between an open position in which the inhaler can be used and a closed position in which the inhaler cannot be used.

Other features and/or advantages of the invention will be apparent from detailed description which follows.

BRIEF DESCRIPTION OF THE DRAWINGS

A specific embodiment of the invention will now be described, by way of example only, with reference to the accompanying drawings, in which.

DETAILED DESCRIPTION

The invention provides an inhaler for delivering dry-powder medicament to a patient from an open blister pocket of a blister pack. The blister pack has a plurality of blister pockets spaced apart in a length direction of the pack and each contains a measured dose of the medicament. Thee inhaler comprises a housing for enclosing used and unused portions of the blister pack together with a medicament dispensing mechanism for opening the blister pockets of the blister pack. The inhaler also comprises a manifold through which air can be drawn in use of the inhaler. The manifold comprises an air inlet for receiving external air, at least one medicament aperture for communicating with an opened pocket of the blister pack to enable entrainment of the medicament by the air drawn through the manifold, and an air outlet for delivery of the entrained medicament to the patient. According to the invention, the manifold and a part of the housing are provided as a unitary moulded plastics component which defines, in use of the inhaler, at least a portion of the outer surface of the inhaler in which the air inlet is arranged.

Figure 1:
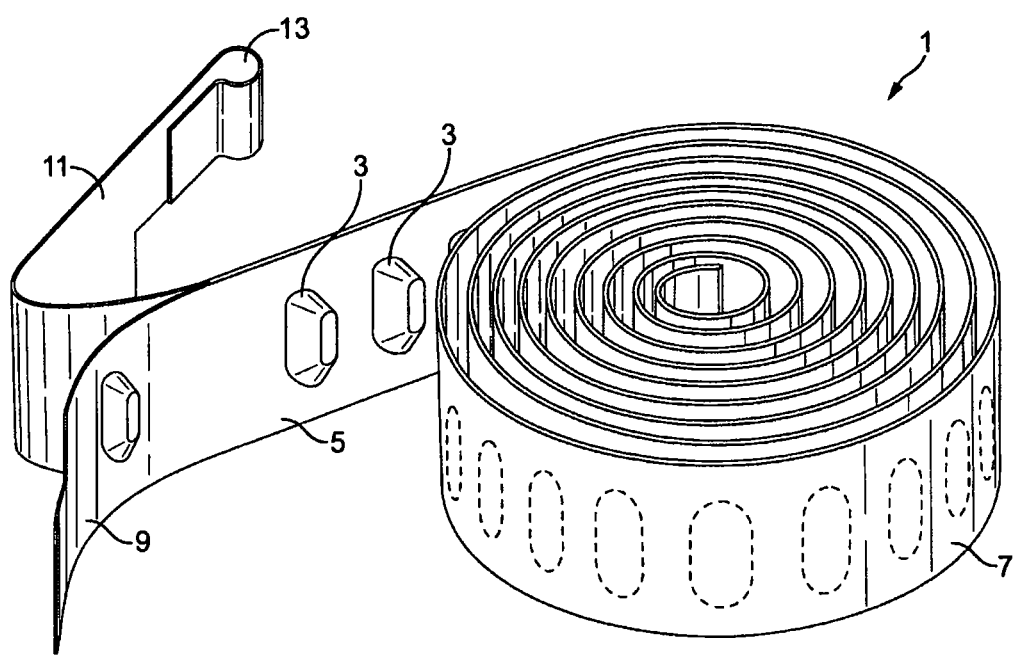
FIG. 1 is a perspective view of a known blister pack for use with a dry-powder inhaler.

FIG. 1 shows a known blister pack 1 which is suitable for use with known dry-powder inhalers and dry-powder inhalers according to the invention. The blister pack 1 is in the form of a flexible elongate strip defining a single row of blister pockets 3 spaced along its length. The blister pack 1 may have, for example, sixty or one hundred blister pockets in total.

The blister pack 1 comprises a base sheet 5 in which recesses each corresponding to a blister pocket 3 are formed and a cover sheet 7 which is hermetically but peelably sealed to the surface of the base sheet 5 surrounding the recesses. The base sheet 5 and the cover sheet 7 are typically formed of laminates comprising plastics and aluminium films. The base sheet 5 is more rigid than the cover sheet 7, and preferably has a rigidity which is sufficient to maintain a predetermined shape of each formed recess. The recesses formed in the base sheet 5 are elongate in shape, with a length direction corresponding to the width direction of the blister pack 1.

The cover sheet 7 is hermetically but peelably sealed to the base sheet 5 by a heat seal lacquer. The cover sheet 7 is sealed to the base sheet 5 over its entire surface except for those portions which overlie the recesses in the base sheet 5 and leading edge portions 9, 11 of the base sheet 5 and the cover sheet 7. As the blister pack 1 is used up, the leading edge portions 9, 11 of the base sheet 5 and the cover sheet 7 lengthen, and these portions are described herein as "used portions". The portion of the blister pack 1 of which the cover sheet 7 has not been peeled away from the base sheet 5 is described herein as the "unused portion". The blister pack 1 is arranged such that the cover sheet 7 can be peeled away from the base sheet 5 is a progressive manner, so that the blister pockets 3 can be opened one at a time.

Each blister pocket 3 of the blister pack 1 comprises an enclosed volume defined by surfaces of the base sheet 5 and the cover sheet 7. The enclosed volume defined by the blisters is generally constant and is filled with a predetermined quantity of dry-powder medicament suitable for inhalation by a patient. In use of the blister pack 1, the leading edge 11 of the cover sheet 7 is peeled away from the base sheet 5 to open the blister pockets 3. The leading edge of the cover sheet 7 is provided with a loop 13 for applying a tension to enable to cover sheet 7 to be peeled away from the base sheet 5.

A more extensive description of the blister pack 1 can be found in U.S. Pat. No. 5,590,645, the entire content of which is incorporated herein by reference.

Figure 2:
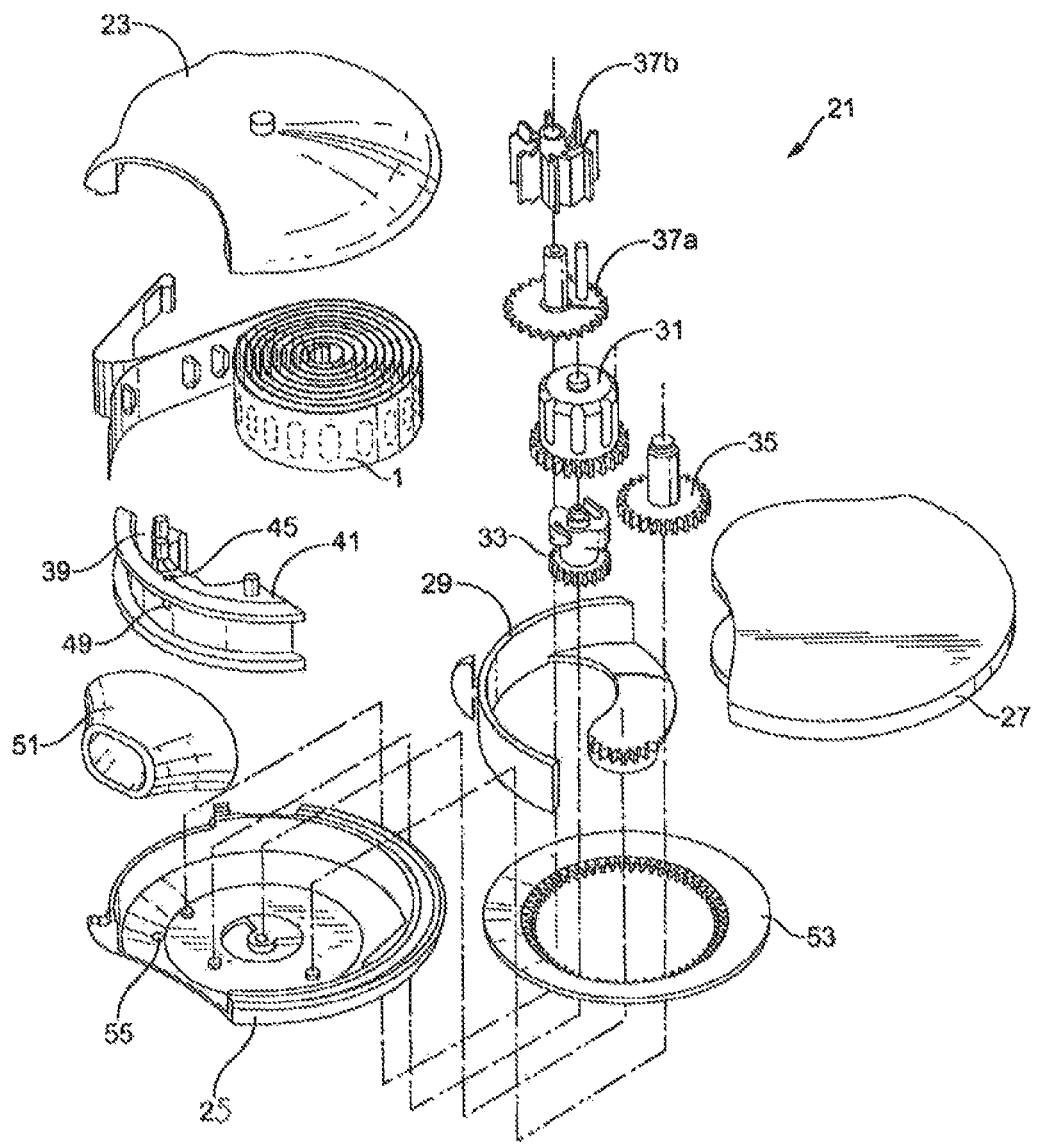
FIG. 2 is an exploded view of a known dry-powder inhaler comprising the blister pack shown in FIG. 1.
Figure 3:
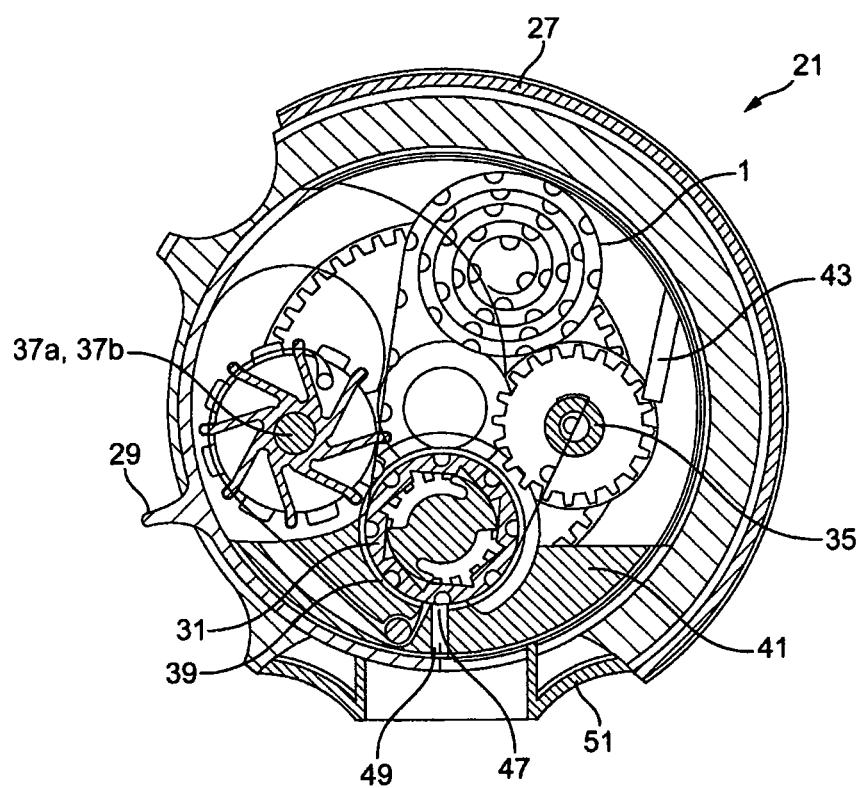
FIG. 3 is a cross-sectional plan view of the dry-powder inhaler shown in FIG. 1 for use in explaining the principle of operation.

FIGS. 2 and 3 show a known dry-powder inhaler 21 which comprises the blister pack 1 shown in FIG. 1. FIG. 2 is an exploded view of the inhaler 21 and FIG. 3 is a cross-sectional plan view of the inhaler 21 for use in explaining its principle of operation.

The inhaler 21 has a disc-like outer shape with rounded edges and a thickness sufficient to accommodate the width of the blister pack 1. As well as the blister pack 1, the inhaler 21 comprises a housing for enclosing used and unused portions of the blister pack 1, a medicament dispensing mechanism for opening the blister pockets 3 of the blister pack 1, a manifold through which air can be drawn in use of the inhaler 21, and a dose counter for counting the number of doses dispensed by or remaining in the inhaler 21.

The inhaler housing comprises a pair of housing members, namely an upper housing member 23 and a lower housing member 25, which snap-fit together to define a significant part of the outer surface of the inhaler 21. The upper and lower housing members 23, 25 also define an internal chamber. The inhaler 21 is additionally provided with a cover 27 which is pivotally mounted to the housing members 23, 25 and is arranged to rotate about the housing between open position of the inhaler 21, as shown in FIG. 3, and a closed position of the inhaler 21 (not shown).

The medicament dispensing mechanism of the inhaler 21 is largely contained within the housing and essentially includes means for peeling the cover sheet 7 from the base sheet 5 of the blister pack 1 to open a blister pocket 3, and means for indexing the longitudinal position of the blister pack 1 by a distance equal to the longitudinal pitch between blister pockets 3, so as to bring the newly opened blister pocket 3 containing dry-powder medicament into alignment with the manifold (described below) to enable inhalation by the patient.

The medicament dispensing mechanism comprises a pivotally mounted trigger 29 having a finger tab, a blister pack indexing wheel 31 mounted about an indexing ratchet wheel 33, a base sheet winding wheel 35, a cover sheet winding wheel 37a, 37b, and a guide surface 39 for guiding the cover sheet-side of the blister pack 1. The guide surface 39 is defined by a moulded plastics component 41 and includes a peeling edge for separating the cover sheet 7 from the base sheet 5 of the blister pack 1.

The mechanism also comprises a pawl 43 attached to the housing for engaging teeth of the base sheet winding wheel 35 to prevent anticlockwise (backwards) rotation.

The cover sheet winding wheel 37a, 37b comprises a first part in the form of a toothed wheel 37a having protruding axial and non-axial parallel shafts and a second part in the form of a wheel 37b having a hollow shaft provided with resilient wings extending outwardly from the shaft. The protruding shaft of the wheel 37a engages with the hollow shaft of the wheel 37b such that one wheel cannot be rotated relative to the other.

The manifold is defined by the same moulded plastics component 41 that defines the guide surface 39 of the medicament dispensing mechanism. The manifold includes an air inlet 45 for receiving air from within the housing, a medicament aperture 47 for communicating with the internal chamber defined by the housing and through which entrained medicament is drawn, and an air outlet 49 for delivery of the entrained medicament to the patient. The air outlet 49 is in communication with a mouthpiece provided with a mouthpiece insert 51.

The dose counter of the inhaler comprises a display aperture 55 formed in the lower housing member 25 and a display element in the form of a display ring 53 provided with dose counting indicia and arranged such that a succession of the indicia are sequentially visible through the display aperture as the display ring 53 is rotated about an axis of the disc-like outer shape of the inhaler 21. An inner edge of the display ring 53 is provided with teeth for rotationally driving the display ring 53.

The blister pack 1 is arranged within the inhaler 21 such that an unused portion is loosely coiled within the internal chamber defined by the housing. The leading edge of the cover sheet 7 is attached to the non-axial shaft of the cover sheet winding wheel 37a by its loop 13 and the used portion of the cover sheet 7 is wound around the resilient wings of the cover sheet winding wheel 37b. The used portion of the base sheet 5 is loosely wound around the base sheet winding wheel 35.

The portion of the blister pack 1 at which the cover sheet 7 separates from the base sheet 5 is arranged such that the recesses of the base sheet 5, which read through to the other side of the base sheet 5 as protrusions, are received in circumferentially spaced recesses in the surface of the indexing wheel 31. The recesses of the base sheet 5 are maintained within the recesses of the indexing wheel 31 by the guide surface 39 acting on the cover sheet-side of the blister pack 1. The used portion of the base sheet 5 extends in front of the medicament aperture 47 of the manifold in a direction towards the base sheet winding wheel 35 and the used portion of the cover sheet 7 passes between the peeling edge of the guide surface 39 and the outer side surface of the manifold in a direction towards the cover sheet winding wheel 37a, 37b.

In use of the known inhaler 21, the patient moves the cover 27 to the open position in which the mouthpiece insert 51 is exposed, as shown in FIG. 3. The patient then presses the finger tab of the trigger 29 to rotate a set of teeth formed on an arcuate surface thereof. The teeth of the trigger 29 engage circumferential teeth formed on the indexing ratchet wheel 33, rotation of which causes rotation of the indexing wheel 31. Rotation of the indexing wheel 31 also causes rotation of the base sheet winding wheel 35, the lid sheet winding wheel 37a, 37b and the display ring 53 of the dose counter.

The rotation of the cover sheet winding wheel 37a, 37b, applies a tension to the used portion of the cover sheet 7 which is sufficient to peel a portion of the cover sheet 7 from the base sheet 5 of the blister pack to thereby open a blister pocket 3 containing a dose of dry-powder medicament. At the same time, the indexing wheel 31 is rotated by an angle sufficient to longitudinally index the blister pack 1 by a distance equal to the pitch between blister pockets 3 to thereby move the opened blister pocket 3 into registration with the medicament aperture 47 of the manifold.

The rotation of the display ring 53 of the dose counter causes a dose counting indicium to be incremented, to thereby inform the patient that a dose has been dispensed.

The patient can then inhale the dose of dry-powder medicament by inhaling through the mouthpiece to draw air through the air inlet 45 of the manifold, which air passes through the medicament aperture 47 to entrain the medicament, and is delivered to the patient via the air outlet 49.

After use of the inhaler 1, the cover 27 is rotated back the closed position (not shown) to reset the medicament dispensing mechanism in preparation for a subsequent use.

Inhalers of the type described above are described in more detail in the aforementioned U.S. Pat. No. 5,590,645.

The known inhaler described above is satisfactory in many respects. In particular, the use of a peelable blister pack enables the moisture content of the dry-powder medicament to be carefully controlled and this, in combination with the peeling-type medicament dispensing mechanism provides consistent dose sizes. However, there remains a need for an improved dry-powder inhaler.

Figure 4:
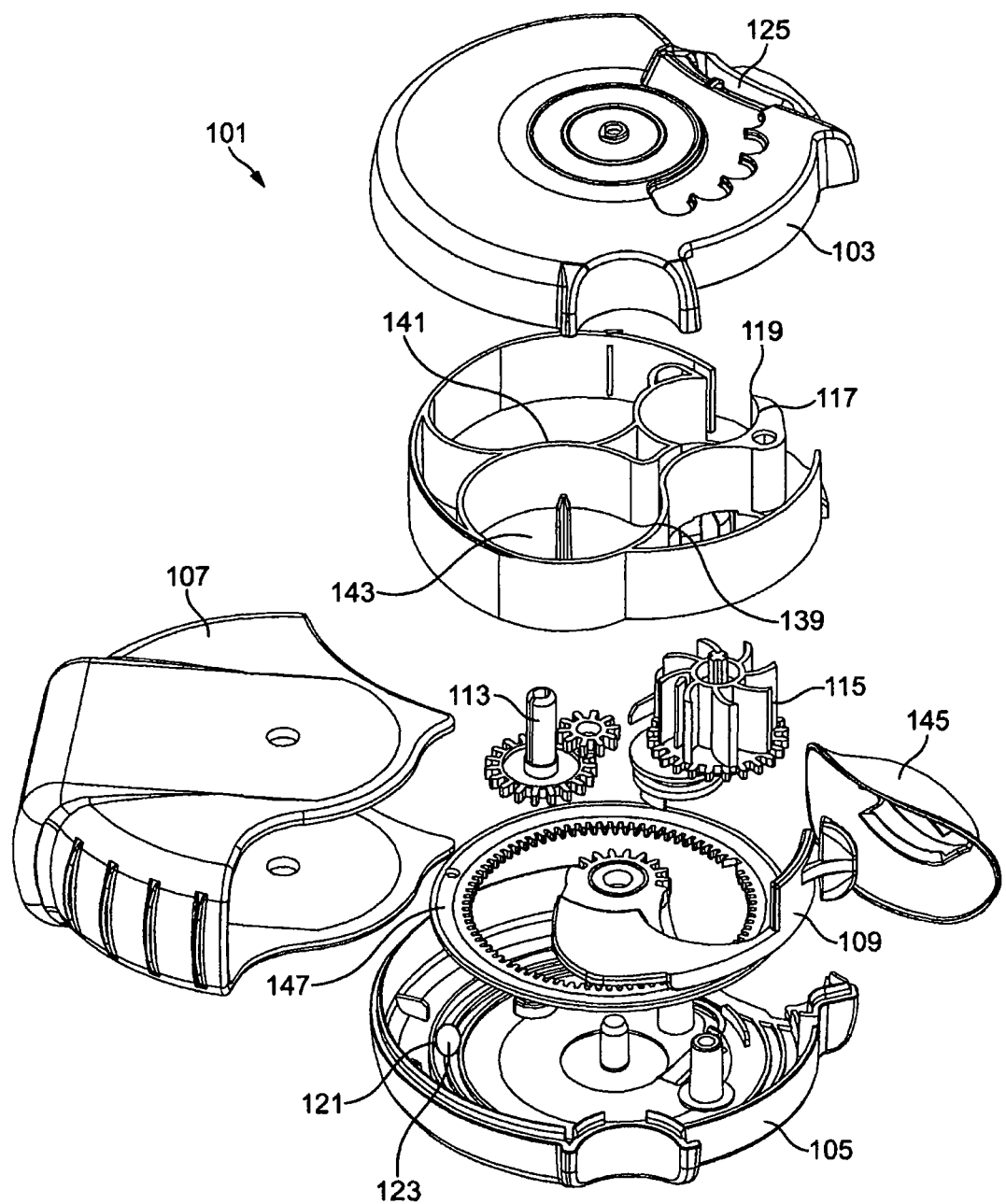
FIG. 4 is an exploded view of a dry-powder inhaler according to the invention, with some components of the inhaler omitted for clarity.
Figure 5:
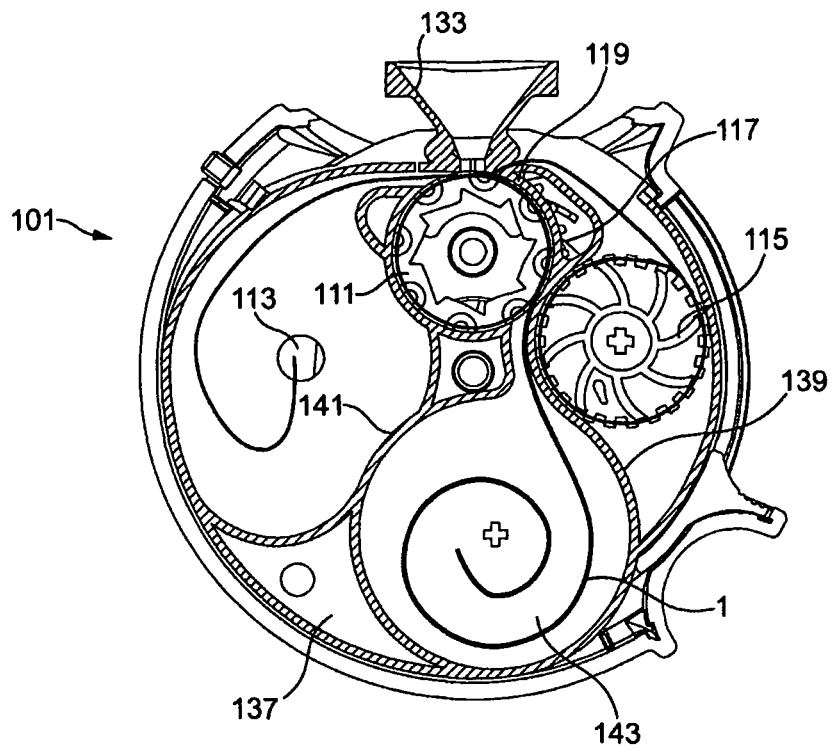
FIG. 5 is a cross-sectional plan view of the dry-powder inhaler shown in FIG. 4 for use in explaining the principle of operation.
Figure 6:
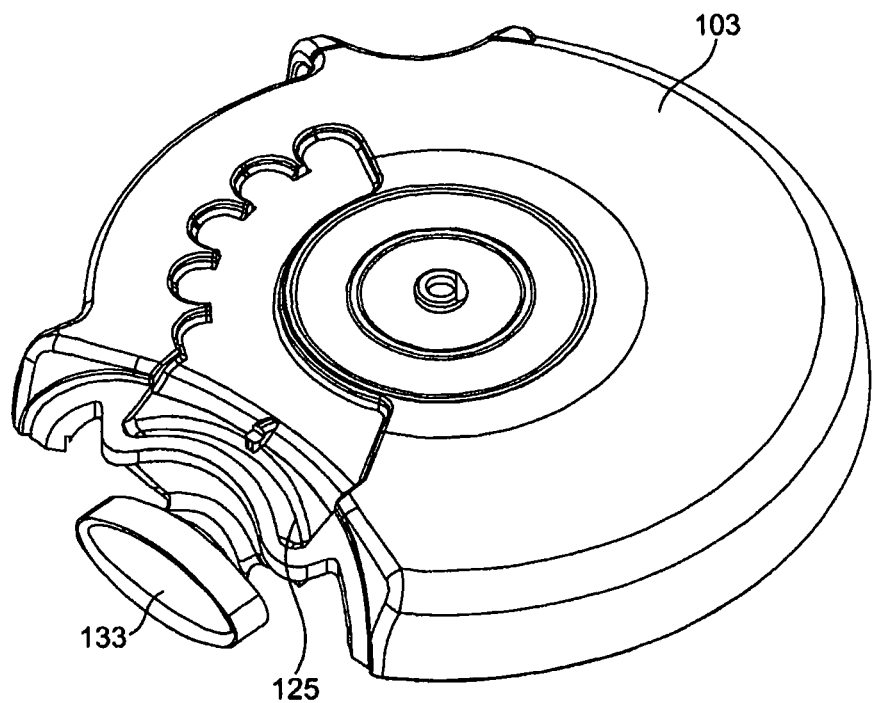
FIGS. 6 and 7 are different perspective views of an outer housing member of the dry-powder inhaler shown in FIG. 4.
Figure 7:
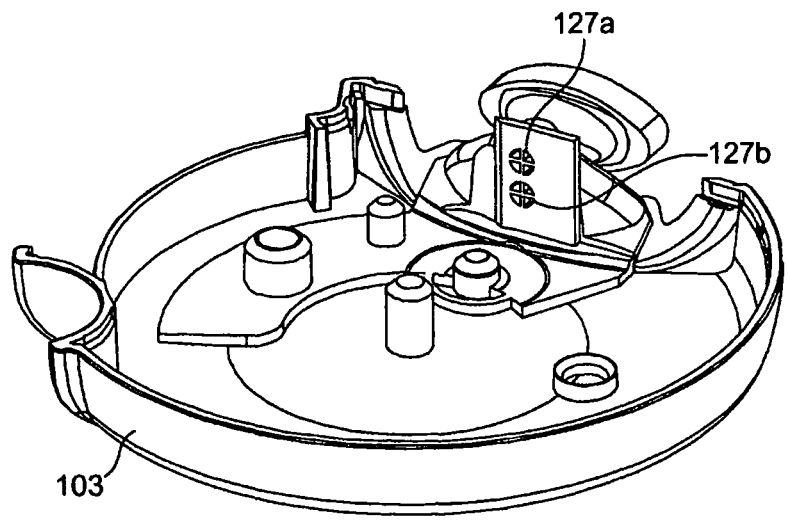
Figure 8:
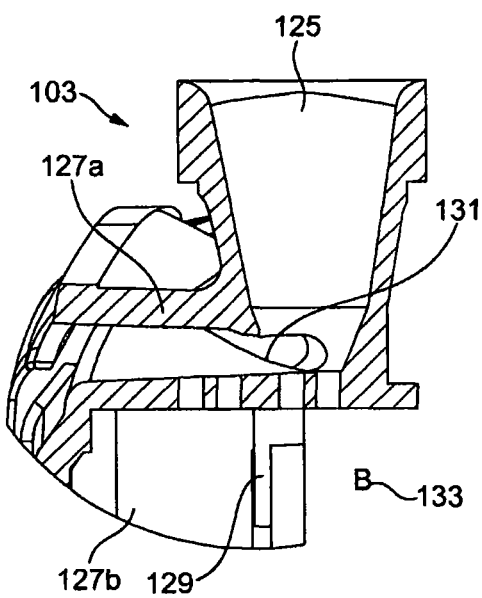
FIG. 8 is an enlarged fragment of a cross-sectional side view of the outer housing member shown in FIGS. 6 and 7.
Figure 9:
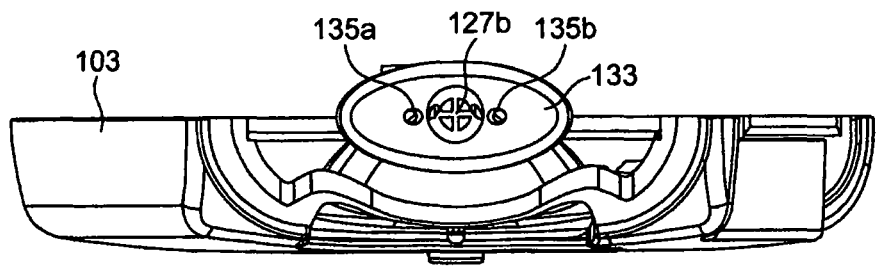
FIG. 9 is a front view of the outer housing member shown in FIGS. 6 and 7.
Figure 10:
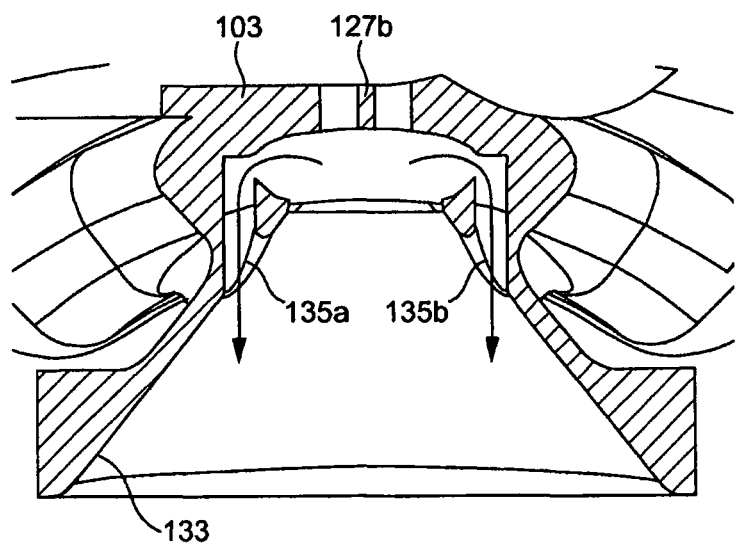
FIG. 10 is an enlarged fragment of a cross-sectional plan view of the outer housing member shown in FIGS. 6 and 7.
Figure 11:
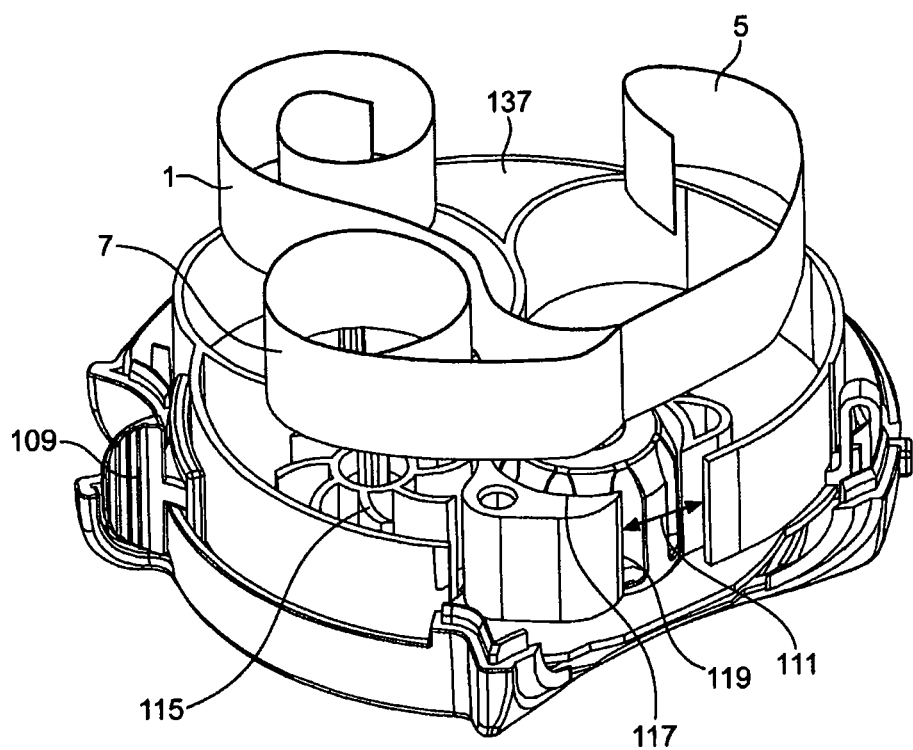
FIG. 11 is a perspective view of certain components of the dry-powder inhaler shown in FIG. 4 for use in explaining its method of assembly.

FIGS. 4 to 11 show a dry-powder inhaler 101 according to the invention, which inhaler comprises the blister pack 1 shown in FIG. 1. FIG. 4 is an exploded view the inhaler 101, with some components of the inhaler omitted for clarity. FIG. 5 is a cross-sectional plan view of the inhaler 101. FIGS. 6 and 7 are different perspective views of an outer housing member of the inhaler 101. FIG. 8 is an enlarged fragment of a cross-sectional side view of the outer housing member. FIG. 9 is a front view of the outer housing member. FIG. 10 is an enlarged fragment of a cross-sectional plan view of the outer housing member. FIG. 11 is a perspective view of certain components of the inhaler 101.

The inhaler 101 according to the invention is similar in many respect to the known inhaler 21 described above. Aspects of the inhaler 101 which are not specifically described below should be taken to be the same or similar to those described above.

Accordingly, with specific reference to FIGS. 4 and 5, the inhaler 101 according to the invention has an outer shape with rounded edges and a thickness sufficient to accommodate the width of the blister pack 1. The inhaler comprises the blister pack 1 described above, a housing for enclosing used and unused portions of the blister pack 1, a medicament dispensing mechanism for opening the blister pockets 3 of the blister pack 1, a manifold through which air can be drawn in use of the inhaler 101, and a dose counter for counting the number of doses dispensed by or remaining in the inhaler 101.

The inhaler housing comprises a pair of outer housing members, namely an upper member 103 and a lower member 105 which snap-fit together to define a significant part of the outer surface of the inhaler 101. The upper and lower housing members 103, 105 also define an internal chamber. The inhaler 101 is additionally provided with a pivotably mounted cover 107 arranged to rotate about the housing between open and closed positions.

The medicament dispensing mechanism of the inhaler 101 is largely contained within the housing and includes means for peeling the cover sheet 7 from the base sheet 5 of the blister pack 1 to open a blister pocket 3, and means for indexing the longitudinal position of the blister pack 1.

More particularly, the medicament dispensing mechanism comprises a pivotally mounted trigger 109 having a finger tab, a blister pack indexing wheel 111, a base sheet winding wheel 113, a cover sheet winding wheel 115, and a guide surface 117 for guiding the cover sheet-side of the blister pack 1. The guide surface 117 includes a peeling edge 119 for separating the cover sheet 7 from the base sheet 5 of the blister pack 1.

The dose counter of the inhaler 101 comprises a display aperture 121 formed in the lower outer housing member 105 and a display element in the form of a display ring 147 provided with dose counting indicia and arranged such that a succession of the indicia are sequentially visible through the display aperture 121 as the display ring 147 is rotated about an axis of the outer shape of the inhaler 101. The dose counting indicia comprise Arabic numerals which count down from the numeral "60" to the numeral "0" in increments of one to indicate the number of doses remaining in the inhaler 101.

An inner edge of the display ring 147 is provided with teeth for rotationally driving the display ring 147, which teeth are driven by a gear train coupled to the medicament dispensing mechanism. The gear train is arranged so that the indicium visible through the display aperture 121 is incremented each time the medicament dispensing mechanism is actuated.

The display aperture 121 formed in the upper outer housing member 103 is provided with a convex lens 123 which is spaced from the dose counting indicia of the display ring and arranged to magnify the indicia. The convex lens 123 is formed of a transparent plastics material.

By provided the convex lens 123, a patient may more easily observe the dose counting indicia of the dose counter and/or the need for multiple display rings may be avoided (since a larger number of small indicia can be provided on a single ring).

With specific reference to FIGS. 6 to 10, the manifold of the inhaler 101 includes an air inlet 125 for receiving external air, a pair of medicament apertures 127a, 127b for communicating with an opened pocket 3 of the blister pack to enable entrainment of medicament by air drawn through the manifold and an air outlet 129 for delivery of the medicament to the patient. The air inlet 125 defines the sole point of entry for external air into the inhaler 101.

According to the invention, the manifold is formed as part of the upper outer housing member 103. In other words, the manifold and the upper outer housing member 103 are formed as a unitary component, specifically a unitary moulded plastics component formed of high density polyethylene (HDPE).

In use of the inhaler 101 (that is to say with the cover 107 in the open position), the unitary component defines the part of the outer surface of the inhaler 101 which surrounds the air inlet 125. In other words, the unitary component defines not only the manifold, but also an outer surface of the inhaler in which the air inlet 125 of the manifold is formed. Furthermore, air is drawn into the manifold solely through the air inlet (apart from the air which circulates through the medicament apertures 127a, 127b).

By such an arrangement, the risk of drawing air into the manifold from within the inhaler housing may be reduced. Such air may be contaminated with medicament left over from previous actuations of the medicament dispensing mechanism.

The air inlet 125 of the manifold has an elongate, arcuate cross-section which reduces in length in the direction of the inhaled airflow. The medicament apertures 127a, 127b are provided sequentially in the airflow direction, which direction is parallel to the axis of the outer shape of the inhaler 101 and the width direction of the blister pack 1. A protrusion 131 in the wall of the manifold facing the medicament apertures 127a, 127b is provided to restrict airflow in the manifold between the medicament apertures 127a, 127b. In this way, air drawn through the manifold is directed from the air inlet 125 into an opened blister pocket 3 through the first medicament aperture 127a, and entrained medicament is directed from the opened blister pocket 3 into the manifold through the second medicament aperture 127b.

The unitary component defining the manifold and the upper outer housing member 103 also defines a mouthpiece 133 arranged to receive the entrained medicament from the air outlet 129 of the manifold. The mouthpiece 133 is arranged substantially perpendicular to the manifold such that an axis of the mouthpiece 133 is aligned with the second medicament aperture 127b. Tapered walls of the mouthpiece 133 are provided with airflow diversion holes 135a, 135b which communicate with the manifold and provide an alternative route for air drawn through the manifold, as illustrated by the arrows in FIG. 10. The airflow diversion holes 135a, 135b are arranged such that air therefrom is drawn into the mouthpiece in a direction substantially parallel to the axis of the mouthpiece 133 for preventing excessive spreading of the entrained medicament.

Each of the medicament apertures 127a, 127b is provided with a divider. The dividers serve to deagglomerate the medicament by breaking up the medicament particles.

The mouthpiece 133 is provided with a mouthpiece insert 145 formed of a soft plastics material which provides a comfortable surface against which the patient may seal his lips during use of the inhaler 101.

With reference again to FIGS. 4, 5 and 11, it will be seen that the inhaler 101 also comprises an inner housing member 137. The inner housing member 137 is arranged within the outer housing members 103, 105 and takes to form of a tray-like moulded plastics component having a flat base surface from which transverse walls extend in a direction perpendicular to the base surface (corresponding to the width direction of the blister pack 1). Apertures are provided in the base surface of the inner housing member 137 to enable the proper functioning of elements of the medicament dispensing mechanism. The transverse walls serve to isolate the used portions from the unused portion of the blister pack 1. Thus, a first transverse wall 139 separates the used portion of the of the cover sheet 7 from the unused portion of the blister pack 1 and a second transverse wall 141 separates the used portion of the base sheet 5 from the unused portion of the blister pack 1.

The transverse walls of the inner housing member 137 in effect define separate compartments for accommodating the different portions of the blister pack 1, thereby minimising the risk that residual medicament on the used portions of the base sheet 5 and the cover sheet 7 will contaminate the unused portion of the blister pack 1, which could lead to overdosing.

The inner housing member 137 and the upper outer housing member 103 together define an enclosure 143 which substantially encloses the unused portion of the blister pack 1 to protect it from contamination by residual medicament contained in the inhaler housing.

The inner housing member 137 described above also defines the guide surface 117 of the medicament dispensing mechanism, that is to say the inner housing member 137 and the guide surface 117 are provided as a unitary component.

The blister pack 1 is arranged within the inhaler 101 such that an unused portion is loosely coiled within the enclosure 143 defined by the housing members. The used portion of the cover sheet 7 is wound around the cover sheet winding wheel 115. The used portion of the base sheet 5 is loosely wound around the base sheet winding wheel 113.

The portion of the blister pack 1 at which the cover sheet 7 separates from the base sheet 5 is arranged such that the recesses of the base sheet 5, which read through to the other side of the base sheet 5 as protrusions, are received in circumferentially spaced recesses in the surface of the indexing wheel 111. The recesses of the base sheet 5 are maintained within the recesses of the indexing wheel 111 by the guide surface 117 acting on the cover sheet-side of the blister pack 1. The used portion of the base sheet 5 extends in front of the medicament apertures 127a, 127b of the manifold in a direction towards the base sheet winding wheel 113. The used portion of the cover sheet 7 passes between the peeling edge 119 of the guide surface 117 and the outer side surface of the manifold in a direction towards the cover sheet winding wheel 115.

During assembly of the inhaler 101, the used portion of the cover sheet 7 is threaded through a gap between the peeling edge 119 and the side surface of the manifold and then engaged with the cover sheet winding wheel 115. By providing an inhaler 101 in which the guide surface 117 and the manifold are defined by separate components (namely the inner housing member 137 and the upper outer housing member 103, respectively), the width of the gap between the peeling edge 119 and the manifold in the assembled inhaler can be minimised. In particular, the used portion of the cover sheet 7 may be threaded through the gap prior to assembly of the components 137, 103 and while the gap is relatively wide, and then the components 137, 103 may then be assembled with the blister pack 1 into the inhaler 101 with the gap having a reduced width, for example only marginally wider than the thickness of the cover sheet 7. By minimising the width of the gap, the risk of medicament being lost from an opened blister pocket 3 during use of the inhaler 101, as the blister pocket 3 is moved from the peeling edge 119 into registration with the medicament holes 127a, 127b of the manifold, is minimised. In this way, underdosing (and possible subsequent overdosing) may be avoided.

The inner housing member 137 and the pair of outer housing members 103, 105 comprise means for precisely locating the inner housing member 137 relative to the pair of outer housing members 103, 105. The locating means comprises engagement tabs and recesses (not shown) formed in the inner housing member 137 and the pair of outer housing members 103, 105, the engagement tabs and recesses being arranged to engage with each other to fix the relative locations of the components.

In use of the inhaler 101 according to the invention, the patient moves the cover 107 to the open position in which position the mouthpiece insert 145 is exposed. The patient then presses the finger tab of the trigger 109 to rotate a set of teeth formed on an arcuate surface thereof. The teeth of the trigger 109 engage circumferential teeth formed on an indexing ratchet wheel (not shown), rotation of which causes rotation of the indexing wheel 111. Rotation of the indexing wheel 111 also causes rotation of the base sheet winding wheel 113, the lid sheet winding wheel 115 and the display ring of the dose counter (not shown).

The rotation of the cover sheet winding wheel 115, applies a tension to the used portion of the cover sheet 7 which is sufficient to peel a portion of the cover sheet 7 from the base sheet 5 of the blister pack to thereby open a blister pocket 3 containing a dose of dry-powder medicament. At the same time, the indexing wheel 111 is rotated by an angle sufficient to longitudinally index the blister pack 1 by a distance equal to the pitch between blister pockets 3 to thereby move the opened blister pocket 3 into registration with the medicament apertures 127a, 127b of the manifold.

The rotation of the display ring of the dose counter causes a dose counting indicia to be incremented, to thereby inform the patient that one dose has been dispensed.

The patient can then inhale the dose of dry-powder medicament by inhaling through the mouthpiece 133 to draw air through the air inlet 125 of the manifold, which air passes through the medicament apertures 127a, 127b to entrain the medicament, and is delivered via the air outlet 129 and the mouthpiece 133.

After use of the inhaler 101, the cover 107 is rotated back the closed position to reset the medicament dispensing mechanism in preparation for a subsequent use.

A specific embodiment of the invention has been described above in detail. Various changes to the embodiment may be made without departing from the scope of the invention, as defined by the claims.

The invention claimed is:

1. An inhaler for delivering dry-powder medicament to a patient from an open blister pocket of a blister pack, the blister pack having a plurality of blister pockets spaced apart in a length direction of the pack and each containing a measured dose of the medicament, the inhaler comprising:
   a housing for enclosing used and unused portions of the blister pack together with a medicament dispensing mechanism for opening the blister pockets of the blister pack; and
   a manifold through which air can be drawn in use of the inhaler, the manifold comprising an air inlet for receiving external air, at least one medicament aperture for communicating with an opened pocket of the blister pack to enable entrainment of the medicament by air drawn through the manifold, and an air outlet for delivery of the entrained medicament to the patient,
   wherein the manifold and a part of he housing are provided as a unitary moulded plastics component,
   wherein the unitary component defines, in use, at least a portion of he outer surface of the inhaler in which the air inlet is arranged, and
   wherein the at least one medicament aperture is provided with at least one obstacle for de-agglomerating the entrained medicament.

2. An inhaler according to claim 1, wherein the manifold is arranged such that, in use, air is drawn into the manifold solely through the air inlet.

3. An inhaler according to claim 1, wherein the air inlet of the manifold defines a sole point for entry for external air into the inhaler.

4. An inhaler according to claim 1, wherein the air inlet of the manifold has an elongate cross-sectional shape, and wherein the cross-sectional area of the manifold reduces in the airflow direction.

5. An inhaler according to claim 1, wherein the unitary component further defines a mouthpiece arranged to receive, in use, the entrained medicament from the air outlet of the manifold.

6. An inhaler according to claim 5, wherein the manifold and the mouthpiece are arranged such that the airflow direction in the mouthpiece is substantially perpendicular to the airflow direction in the manifold and a bend in the airflow is located adjacent to the at least one medicament aperture, such that entrained medicament can be delivered to the patient from the opened blister pocket along a substantially straight path.

7. An inhaler according to claim 5, wherein the cross-sectional area of the mouthpiece increases in the airflow direction.

8. An inhaler according to claim 1, wherein the unitary component is formed of a moulded plastics material.

9. An inhaler according to claim 8, wherein the unitary component is formed of a material selected from the group consisting of polyolefins, including polyethylene, high density polyethylene (HDPE), and polypropylene; polyesters, including polyethylene terephthalate; polyamides, including nylons; thermosetting polymers, including urea-formaldehyde, melamine, epoxy resins and polyimides; and mixtures or copolymers thereof.

10. An inhaler according to claim 1, further comprising a cover rotatable between an open position in which the inhaler can be used and a closed position in which the inhaler cannot be used.

11. An inhaler according to claim 1, wherein the housing comprises a pair of outer housing members defining an outer shape of the inhaler, and wherein one of the pair of outer housing members is the unitary component.

12. An inhaler according to claim 11, further comprising a dose counter, wherein the dose counter comprises:
- a display aperture formed in one of the pair of outer housing members;
- a display element having dose counting indicia, the display element being rotatably mounted inside the housing such that a succession of the dose counting indicia are sequentially visible through the display aperture as the display element is rotated about an axis of the outer shape of the inhaler; and
- a driving means for incrementally rotating the display element in response to actuation of the medicament dispensing mechanism, wherein the display aperture formed in the outer housing member is provided with a magnifying lens arranged to magnify the dose counting indicia of the display element.

13. An inhaler according to claim 12, wherein the magnifying lens is a convex lens.

14. An inhaler according to claim 12, wherein the magnifying lens is formed of a transparent plastics material.

15. An inhaler according to claim 12, comprising no more than one rotatably mounted display element having dose counting indicia.

16. An inhaler according to claim 12, wherein the dose counting indicia of the display element include a unique indicium for display after each and every actuation of the medicament dispensing mechanism.

17. An inhaler according to claim 12, wherein the dose counting indicia of the display element comprise at least 10 unique dose counting indicia.

18. An inhaler according to claim 12, wherein the dose counting indicia comprise numerals.

19. An inhaler according to claim 12, wherein each dose counting indicia is representative of a number of doses dispensed by or remaining in the inhaler.

20. An inhaler according to claim 11, wherein the housing further comprises an inner housing member arranged within the pair of outer housing members.

21. An inhaler according to claim 20, further comprising the medicament dispensing mechanism for opening the blister pockets of the blister pack.

22. An inhaler according to claim 21, further comprising the blister pack, wherein each blister pocket contains a measured dose of a dry-powder medicament.

23. An inhaler according to claim 21, for delivering medicament from a blister pack in the form of a flexible elongate strip comprising a base sheet having a plurality of recesses spaced along its length and a cover sheet peelably sealed to the base sheet to define the plurality of blister pockets, wherein the medicament dispensing mechanism comprises means for peeling the cover sheet away from the base sheet of the blister pack.

24. An inhaler according to claim 23, wherein the medicament dispensing mechanism comprises means for longitudinally indexing the blister pack in response to each actuation of the medicament dispensing mechanism, the blister pack being indexed by a distance equal to a pitch between blister pockets, such that each actuation causes a blister to be brought into registration with the at least one medicament aperture of the manifold.

25. An inhaler according to claim 24, wherein the means for indexing comprises a driven indexing wheel having recesses adapted to receive the base sheet of the blister pack, the driven indexing wheel being arranged to turn by a predetermined angle in response to each actuation of the medicament dispensing mechanism.

26. An inhaler according to claim 24, further comprising a trigger for actuating the medicament dispensing mechanism.

27. An inhaler according to claim 23, wherein the medicament dispensing mechanism comprises a driven cover sheet winding wheel for winding up a used portion of the cover sheet.

28. An inhaler according to claim 27, wherein the cover sheet winding wheel is arranged to apply a tension to the used portion of the cover sheet, and wherein the medicament dispensing mechanism further comprises a guide surface for guiding the cover sheet of the unused portion of the blister pack, an end of the guide surface being arranged adjacent to an outer side surface of the manifold and defining a peeling edge, such that, in use, the cover sheet is peeled away from the base sheet at the peeling edge and the used portion of the cover sheet passes between the peeling edge and the outer side surface of the manifold, and an opened blister pocket moves into registration with the at least one medicament aperture of the manifold, wherein the guide surface is defined by the inner housing member, such that the manifold and the guide surface are defined by separate components of the inhaler.

29. An inhaler according to claim 28, wherein the inner housing member and the pair of outer housing members comprise means for locating the inner housing member relative to the pair of outer housing members.

30. An inhaler according to claim 29, wherein the means for locating comprises engagement tabs and recesses formed in the inner housing member and the pair of outer housing members, the engagement tabs and recesses being arranged to engage with each other to fix the location of the inner housing member relative to the pair of outer housing members.

31. An inhaler according to claim 27, wherein the inner housing member defines internal transverse walls extending in a width direction of the blister pack for isolating the used portion of the cover sheet from an unused portion of the blister pack.

32. An inhaler according to claim 31, wherein the medicament dispensing mechanism further comprises a driven base sheet winding wheel for winding up the used portion of the base sheet, and wherein the inner housing member further defines internal transverse walls extending in the width direction of the blister pack for isolating the used portion of the base sheet from the unused portion of the blister pack.

33. An inhaler according to claim 31, wherein the internal transverse walls of the inner housing member define separate compartments for accommodating the used portion of the cover sheet and the used portion of the base sheet, the separate compartments being arranged to contain loose medicament.

34. An inhaler according to claim 33, wherein the internal transverse walls of the inner housing member further define a separate compartment for accommodating the unused portion of the blister pack.

35. An inhaler according to claim 31, wherein the internal transverse walls extend in a perpendicular direction from a base surface of the inner housing member, the base surface of the inner housing member being arranged to support a side edge of the unused portion of the blister pack.

36. An inhaler according to claim 25, wherein one of the pair of outer housing members is arranged to support an opposite side edge of the unused portion of the blister pack.

37. An inhaler according to claim 33, wherein surfaces of the inner housing member and one of the pair of outer housing members are arranged to substantially enclose the unused portion of the blister pack.

38. An inhaler for delivering dry-powder medicament to apatient from an open blister pocket of a blister pack, the blister pack having a plurality of blister pockets spaced apart in a length direction of the pack and each containing a measured dose of the medicament, the inhaler comprising:
 a housing for enclosing used and unused portions of the blister pack together with a medicament dispensing mechanism for opening the blister pockets of the blister pack; and
 a manifold through which air can be drawn in use of the inhaler, the manifold comprising an air inlet for receiving external air, at least one medicament aperture for communicating with an opening pocket of the blister pack to enable entrainment of the medicament by air drawn through the manifold, and an air outlet for delivery of the entrained medicament to the patient,
 wherein the manifold and a part of the housing are provided as a unitary moulded plastics component,
 wherein the unitary component defines, in use, at least a portion of the outer surface of the inhaler in which the air inlet is arranged, and
 wherein the manifold comprises at least two medicament apertures arranged sequentially in an airflow direction of the manifold, a first medicament aperture for the flow of air from the manifold into the opened blister pocket and a second medicament aperture for the flow of the entrained medicament from the opened blister pocket into the manifold.

39. An inhaler according to claim 38, wherein the geometry of the manifold is adapted to direct air from the air inlet into the opened blister pocket through the first medicament aperture and to direct the entrained medicament from the opened blister pocket into the manifold through the second medicament aperture.

40. An inhaler according to claim 39, wherein the geometry of the manifold is so adapted by providing means for restricting airflow in the manifold between the first and second medicament apertures.

41. An inhaler according to claim 40, wherein the means for restricting airflow comprises a localised reduction in the cross-sectional area of the manifold.

42. An inhaler for delivering dry-powder medicament to a patient from an open blister pocket of a blister pack, the blister pack having a plurality of blister pockets spaced apart in a length direction of the pack and each containing a measured dose of the medicament, the inhaler comprising:
 a housing for enclosing used and unused portions of the blister pack together with a medicament dispensing mechanism for opening the blister pockets of the blister pack; and
 a manifold through which air can be drawn in use of the inhaler, the manifold comprising an air inlet for receiving external air, at least one medicament aperture for communicating with an opened pocket of the blister pack to enable entrainment of the medicament by air drawn through the manifold, and an air outlet for delivery of the entrained medicament to the patient,
 wherein the manifold and a part of the housing are provided as a unitary moulded plastics component,
 wherein the unitary component defines, in use, at least a portion of the outer surface of the inhaler in which the air inlet is arranged,
 wherein the unitary component further defines a mouthpiece arranged to receive, in use, the entrained medicament from the air outlet of the manifold, and
 wherein tapered walls of the mouthpiece are provided with a plurality of airflow diversion holes, and wherein the airflow diversion holes are in fluid communication with the manifold such that, in use, air from the manifold is drawn through the airflow diversion holes.

43. An inhaler according to claim 42, wherein the airflow diversion holes are arranged such that, in use, air is drawn through the holes in a direction substantially parallel to a central axis of the mouthpiece for preventing excessive transverse spreading of the entrained medicament in the mouthpiece.

* * * * *

UNITED STATES PATENT AND TRADEMARK OFFICE
CERTIFICATE OF CORRECTION

PATENT NO.        : 8,931,479 B2
APPLICATION NO.   : 13/321077
DATED             : January 13, 2015
INVENTOR(S)       : Johan René Keegstra et al.

Page 1 of 1

It is certified that error appears in the above-identified patent and that said Letters Patent is hereby corrected as shown below:

In the Claims,

At Column 14, Line 29, "of he housing" should read --of the housing--;

At Column 14, Line 32, "of he outer surface" should read --of the outer surface--;

At Column 17, Line 3, "claim 25" should read --claim 35--; and

At Column 17, Line 11, "apatient" should read --a patient--.

Signed and Sealed this
Nineteenth Day of May, 2015

Michelle K. Lee
*Director of the United States Patent and Trademark Office*